(12) United States Patent
Selker et al.

(10) Patent No.: US 11,986,787 B2
(45) Date of Patent: *May 21, 2024

(54) DISPOSABLE BIOREACTOR SYSTEMS AND RELATED METHODS

(71) Applicant: Finesse Solutions, Inc., Santa Clara, CA (US)

(72) Inventors: Mark D. Selker, Los Altos Hills, CA (US); Barbara Paldus, Atherton, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 17/034,575

(22) Filed: Sep. 28, 2020

(65) Prior Publication Data

US 2021/0008512 A1    Jan. 14, 2021

Related U.S. Application Data

(63) Continuation of application No. 15/828,324, filed on Nov. 30, 2017, now Pat. No. 10,821,409, which is a
(Continued)

(51) Int. Cl.
*B01F 3/04* (2006.01)
*B01F 11/00* (2006.01)
(Continued)

(52) U.S. Cl.
CPC ........ *B01F 31/25* (2022.01); *B01F 23/23121* (2022.01); *B01F 31/22* (2022.01);
(Continued)

(58) Field of Classification Search
CPC .... B01F 31/25; B01F 23/23121; B01F 31/22; B01F 31/23; B01F 35/51; B01F 35/513;
(Continued)

(56) References Cited

U.S. PATENT DOCUMENTS 2,884,236 A   4/1959   Maille
3,677,711 A   7/1972   Bond
(Continued)

FOREIGN PATENT DOCUMENTS

GB          1597845 A    9/1981
WO       2005/049784    6/2005

OTHER PUBLICATIONS

Kadarusman, J. et al., "rowing Cholesterol-Dependent NSO Myeloma Cell Line in the Wave Bioreactor System: Overcoming Cholesterol-Polymer Interaction by Using Pretreated Polymer or Inert Fluorinated Ethylene Propylene," Biotechnology Progress, 2005, vol. 21, No. 4, pp. 1341-1346.

(Continued)

*Primary Examiner* — Liban M Hassan
(74) *Attorney, Agent, or Firm* — Mintz Levin Cohn Ferris Glovsky and Popeo, P.C.

(57) ABSTRACT

A method for enhancing mixing and aeration of a liquid reaction medium in a toroidal bioreactor vessel includes dispensing a liquid reaction medium into an interior of a toroidal bioreactor vessel, the interior being bounded by an inner surface, a textured surface being arranged on at least a portion of the inner surface, the textured surface having a plurality of upstanding protuberances. The toroidal bioreactor vessel is rotated in an orbital motion such that there is a resonant frequency traveling wave of the fluid orbiting in one direction in the interior of the toroidal bioreactor vessel when a particular orbital speed is imparted to the toroidal bioreactor vessel.

12 Claims, 5 Drawing Sheets

Related U.S. Application Data continuation of application No. 12/008,447, filed on Jan. 10, 2008, now Pat. No. 9,868,095.

(60) Provisional application No. 60/927,274, filed on May 2, 2007.

(51) Int. Cl.

| | | |
|---|---|---|
| *B01F 15/00* | (2006.01) | |
| *B01F 23/231* | (2022.01) | |
| *B01F 31/22* | (2022.01) | |
| *B01F 31/23* | (2022.01) | |
| *B01F 31/25* | (2022.01) | |
| *B01F 35/51* | (2022.01) | |
| *B01F 35/513* | (2022.01) | |
| *B01F 35/53* | (2022.01) | |
| *C12M 1/00* | (2006.01) | |
| *C12M 3/04* | (2006.01) | |
| *C12M 3/06* | (2006.01) | |

(52) U.S. Cl.
CPC .............. *B01F 31/23* (2022.01); *B01F 35/51* (2022.01); *B01F 35/513* (2022.01); *B01F 35/53* (2022.01); *B01F 35/531* (2022.01); *C12M 23/02* (2013.01); *C12M 23/28* (2013.01); *C12M 27/10* (2013.01); *C12M 27/16* (2013.01); *C12M 27/20* (2013.01)

(58) Field of Classification Search
CPC ....... B01F 35/53; B01F 35/531; C12M 23/02; C12M 23/28; C12M 27/10; C12M 27/16; C12M 27/20
See application file for complete search history.

(56) References Cited

U.S. PATENT DOCUMENTS

| | | | |
|---|---|---|---|
| 4,960,706 A | | 10/1990 | Bliem et al. |
| 5,026,649 A | | 6/1991 | Lyman et al. |
| 5,151,366 A | | 9/1992 | Serkes et al. |
| 5,375,927 A | | 12/1994 | Hermsen et al. |
| 5,939,313 A | | 8/1999 | Cheng |
| 6,130,080 A | * | 10/2000 | Fuller .................... C12M 25/00 435/395 |
| 6,190,913 B1 | | 2/2001 | Singh |
| 6,933,144 B2 | | 8/2005 | Cadwell |
| 6,994,111 B2 | | 2/2006 | Cox |
| 7,691,625 B2 | | 4/2010 | Kuwabara |
| 2002/0072113 A1 | | 6/2002 | Barbera-Guillem et al. |
| 2003/0232711 A1 | | 12/2003 | Berit et al. |
| 2004/0110279 A1 | | 6/2004 | Everet |
| 2005/0032206 A1 | | 2/2005 | Hasegawa et al. |
| 2005/0135104 A1 | | 6/2005 | Crabb et al. |
| 2005/0239199 A1 | | 10/2005 | Kunas et al. |
| 2005/0254055 A1 | | 11/2005 | Peng |
| 2005/0272146 A1 | | 12/2005 | Hodge et al. |
| 2006/0035368 A1 | | 2/2006 | Malinge |
| 2008/0274541 A1 | | 11/2008 | Selker et al. |
| 2018/0085722 A1 | | 3/2018 | Selker et al. |

OTHER PUBLICATIONS

Margaritis, A. et al., "*Novel Bioreactor Systems and Their Applications*," Nature Bioechnology, May 1984, pp. 447-453.

Singh, V., "*Disposable Bioreactor for Cell Culture Using Wave-Induced Agitation*," Cytotechnology, Jul. 1999, vol. 30, pp. 149-158.

Kretzmer, G. et al., "*Response of Mammalian Cells to Shear Stress*," Journal of Applied Microbiology and Biotechnology, 1991, vol. 34, No. 5, pp. 613-616.

Corning® Disposable Spinner Flasks, Product Information and Specifications, 2005 (http://www.corning.com/lifesciences/pdf/lp_disposable spinner flask ss.pdf) [Retrieved via https://web.archive.org/web/20060313111057/http://www.corning.com/lifesciences/pdf/lp_disposable_spinner_flask_ss.pdf].

* cited by examiner

DISPOSABLE BIOREACTOR SYSTEMS AND RELATED METHODS

CROSS-REFERENCE TO RELATED APPLICATIONS

This application is a continuation of U.S. patent application Ser. No. 15/828,324, filed Nov. 30, 2017, now U.S. Pat. No. 10,821,409, which is a continuation of U.S. patent application Ser. No. 12/008,447, filed on Jan. 10, 2008, U.S. Pat. No. 9,868,095, which application claims benefit under 35 U.S.C. § 119(e) to U.S. Provisional Patent Application No. 60/927,274, filed May 2, 2007, which applications are herein incorporated by specific reference in their entireties and for all purposes.

BACKGROUND OF THE INVENTION

1. The Field of the Invention

This invention relates to an improved design for a disposable bioreactor vessel suitable for cell culture and fermentation.

2. The Relevant Technology

The increasing popularity of disposable or single use bioreactors for upstream processing has been recently noted in several studies, and can be understood by considering a typical biotech manufacturing facility. The infrastructure required to implement a facility using traditional glass/steel bioreactors is substantial, and the time and expense required to construct it can be immense. The requirement that both the bioreactor itself, and also the ingress and egress tubing, utilize inert materials such as 316L electro-polished stainless steel requires a large initial investment. Additionally, the size and form factor of disposable bioreactor vessels generally lend themselves to easier storage and re-configurability when compared with traditional, rigid glass/steel solutions. Other advantages are the cost and time savings over traditional designs, the reduction in preparation and sterilization time, the reduced need for purified water for cleaning the vessel after a run, and the significantly reduced post run maintenance time. Additionally, single use bioreactors and the associated plastic tubing lend themselves to being re-configured and validated quickly and efficiently as manufacturing or process requirements change. Although a number of different styles of single use bioreactors have been conceived and introduced into the marketplace, two types currently predominate.

The first type of single-use bioreactor is generally referred to as the "pillow" or "rocker" bag style, and is described, for example, in U.S. Pat. No. 6,190,913. This style of bag has been constructed from a variety of different polymeric materials, but low density polyethylene and ethylene/vinyl-acetate copolymers are currently the most popular materials for at least the innermost layer which contacts the aqueous growth medium. This type of disposable bioreactor utilizes a wave motion induced by movement about a single axis to both mix and sparge (aerate) the contents of the bioreactor.

Another style of bioreactor bag is often referred to as a "liner style" and substantially mimics the function and form of a traditional glass/steel bioreactor. A disposable polymeric bag is used as a liner inside a generally cylindrical glass/steel tank and generally uses an impeller to mix the contents of the bioreactor vessel. This type of system has been commercialized by several manufacturers (see e.g., Published US Patent Applications 2005/0272146 and 2005/0239199). The disposable liner type of bioreactor bag has proven popular for process development or pilot runs using growth medium volumes of 25 liters or more.

Both styles of disposable bioreactors have undergone some scrutiny in order to judge their efficacy in comparison to traditional glass/steel bioreactors. However, statistically rigorous analyses are apparently not available to date. Irrespective of the style of the disposable bioreactor, the inner surface of the polymeric bioreactor bag needs to be both biologically inert and also not prone to leaching nutrients from the growth medium or from the polymer into the growth medium (see Kadarusman et. al, *Growing Cholesterol-Dependent NSO Myeloma Cell Line in the Wave Bioreactor System: Overcoming Cholesterol-Polymer Interaction by using Pretreated Polymer or Inert Fluorinated Ethylene Propylene*, Biotechnology Progress, 2005, 21, p. 1341). Additionally, the liner needs to be chemically stable under the optical illumination often used to facilitate cell growth.

Figure 1:
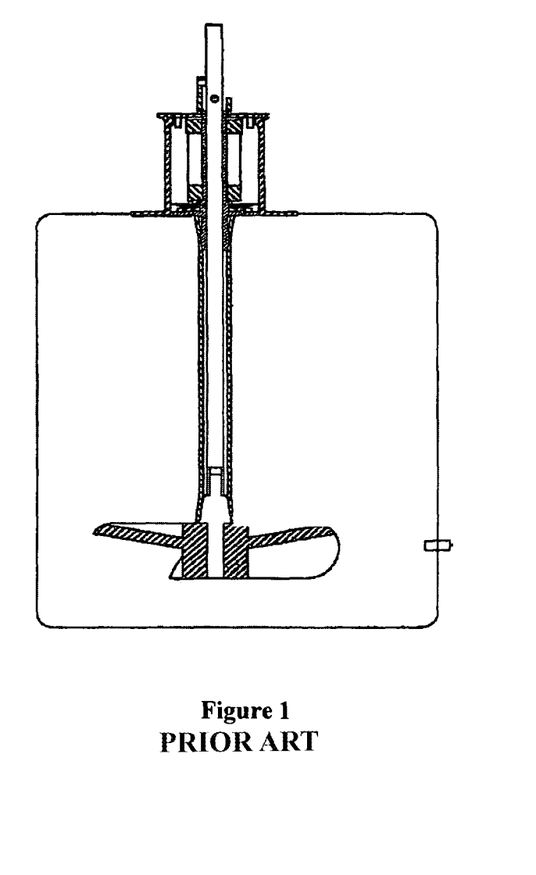
FIG. 1 shows the prior art type of disposable bioreactor system (e.g., HyClone/Thermo-Fisher) that utilizes a disposable polymeric liner and provides structural support for the liner.

Whether a bioreactor is of traditional design or a modern disposable format, the basic function of a bioreactor is to provide a controlled environment in order to achieve optimal growth/product formation in the cell or microbe that is present in the aqueous bioreactor growth medium. The traditional glass and steel bioreactors used in batch processes were proven to be effective in the course of antibiotic production in the 1950's, and still remain the dominant paradigm in the fermentation industry. Criteria for optimizing bioreactor design have been enumerated before (see A. Margaritas and J. B. Wallace, *Novel Bioreactor Systems and Their Applications, Nature Bio/Technology*, May 1984, p. 447.) According to Margaritas et al, some of the basic criteria required to characterize and understand bioreactor performance are:

1. Mass and heat transfer and hydrodynamic characteristics of the bioreactor,
2. Potential for bioreactor scale-up, and
3. Capital and operating costs of the bioreactor Given the extensive existing knowledge regarding the design and performance of traditional glass/steel bioreactors, it was considered desirable to mimic their design as much as possible in the implementation of a disposable bioreactor system. Examination of current products reveals that this approach has been utilized, but with only mixed results. An example of this prior art style of product, as shown in FIG. 1, employs a liner made of a biocompatible, flexible polymeric material set inside a vessel which provides structural support. The end result is a disposable liner which assumes a physical form very similar to that of a traditional (generally cylindrical) bioreactor. The use of an impeller and sparger completes the analogy to a traditional glass/steel vessel. Therefore, the performance of a liner type disposable bioreactor can be measured against the list of criteria 1 through 3 above, and one can get a reasonable idea of the performance through comparison to the performance of similar size and shape traditional glass/steel systems. Given the analogy to known bioreactor shapes and sizes, impeller design and placement, the mixing and oxygenation rates can be approximated. Additionally, traditional scaling arguments can be formulated and implemented, and known techniques of computational fluid mechanics (www.fluent.com) can be applied.

Figure 2:
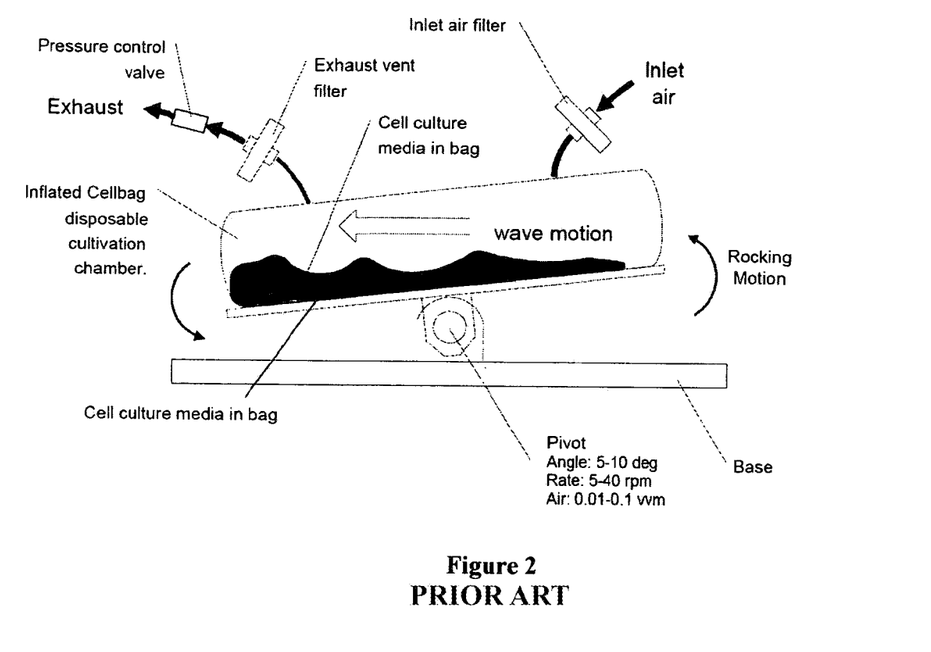
FIG. 2 shows a prior art "pillow" disposable bioreactor bag of flexible polymeric material.

The "pillow" bag style of disposable bioreactor also utilizes bags made of biocompatible films. An example of this design is shown in FIG. 2 (see V. Singh, *Disposable Bioreactor for cell culture using wave-induced agitation*, Cytotechnology 30, 1999, p. 149.). Most proponents of the "pillow" bag stipulate that traditional bioreactors and single-use bioreactors that emulate the traditional glass/steel bioreactor using a disposable liner limit the yield obtainable in mammalian cell growth runs due to impeller induced sheer stress of the cells during mixing and sparging. The "pillow" bag style of disposable bioreactor bag has no impeller, and utilizes a rocking motion to mix and sparge the microorganisms contained within the bag. It is claimed that this rocking motion is gentle on the cells and does not cause sheer stress which can easily damage mammalian cells (G. Kretzmer and K. Schugerl, Journal of Applied Microbiology and Biotechnology, Vol. 34, No. 5, 613-616 (1991)). The boundary conditions set forth by the bag, combined with the rocking motion are alleged to adequately mix and aerate the aqueous culture medium when mammalian cells are used. However, it is not entirely clear that this is the case or that this style of bioreactor is efficacious for non-mammalian cell processes, such as bacterial or microbial fermentations that require more oxygen and/or can have highly viscous contents (reaction medium).

As shown in FIG. 2, the most common commercial versions of the pillow bag style single-use bioreactor utilizes one or more ports on the top of the bag to bring in the air or oxygen, and then utilizes another (output) port in relatively close proximity to the input port to vent the gas(es) produced by the bioprocess. It is likely that in many cases the incoming sparging gas is vented too quickly so that suboptimal oxygenation occurs. For this type of bag, no evidence of an understanding of the performance criteria 1 through 3, as set forth above, is found in the literature. Published data generally indicates that the total cell density achieved in this style of bioreactor is generally less than (and at best, equal to) that achieved in small shaker flasks.

Another style of disposable bioreactor is made by Corning. This product is a disposable or single-use spinner flask. This flask is made of a rigid biocompatible plastic and uses a magnetically driven internal impeller to mix the contents. See (http://www.corning.com/lifesciences/pdtilp disposable spinner flask ss.pdf). However, this design is only suitable for relatively small volume growth processes.

It is an object of the present invention to provide a design for a single-use bioreactor vessel which ensures adequate mixing of the ingredients in the growth medium, and sufficient aeration for cells or microbes which require significant oxygen, but at the same time does not cause destructive shear stress and is scalable to comparatively large volume runs.

BRIEF DESCRIPTION OF THE DRAWINGS

FIG. 4 shows a view of the walls of the preferred embodiment of the bioreactor vessel of FIGS. 3a and 3b where sparging is accomplished through the walls of the vessel.

The walls are shown as corrugated in order to enhance mixing.

DESCRIPTION OF THE INVENTION

The most desirable single-use bioreactor solution would be one that effectively meets criteria 1 through 3, as set forth above, while at the same time requiring the fewest moving parts. Minimizing the number of moving parts will also tend to yield the least expensive and most reliable overall solution. A novel design for a polymeric bioreactor vessel in accordance with the present invention which uses a minimal number of parts is shown in FIGS. 3 through 6.

Figure 3A:
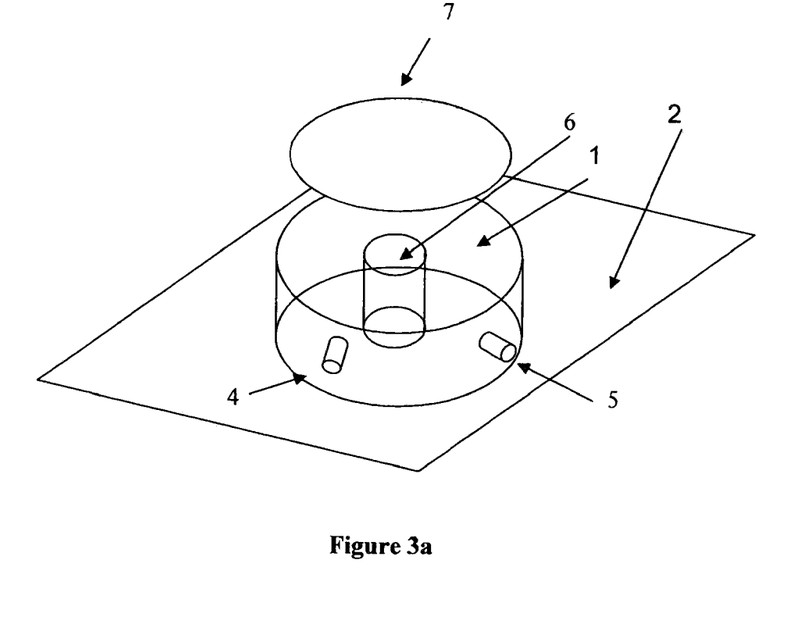
FIG. 3a shows a three-dimensional view of a bioreactor in accordance with the present invention having vertical side walls and which is toroidal in shape.
Figure 3B:
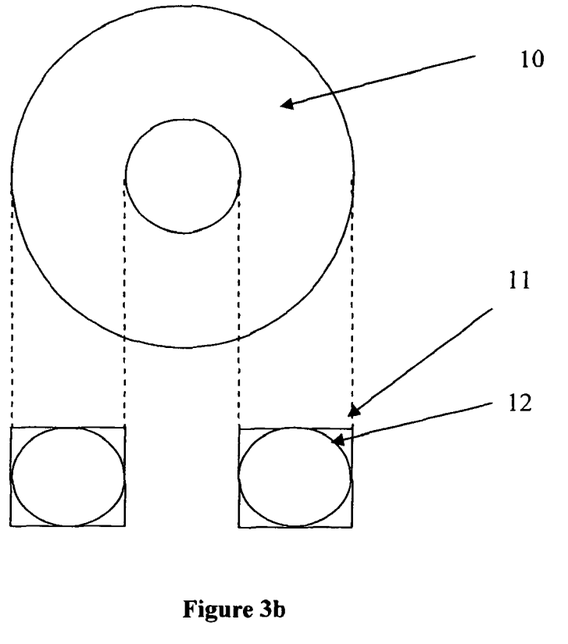
FIG. 3b shows two-dimensional views of a toroidal bioreactor in accordance with the present invention as depicted in FIG. 3a and shows alternative embodiments of the vessel having either a circular (12) or rectangular (11) cross-section.

In FIG. 3a, a cylindrical bioreactor vessel 1 having a substantially rectangular cross-section is shown having a hollow core 6, so that the bioreactor is a toroid. Although the design shown in FIG. 3a is shown as having substantially vertical walls, this is not an essential aspect of the invention and a toroidal (donut) shaped vessel not having vertical surfaces is also suitable, as shown in FIG. 3b in cross section as 12. Alternatively, only one wall (either inner or outer) may be vertical and the other curved.

The vessel can suitably be of a rigid biocompatible polymer. Alternatively, the vessel can be fabricated in whole or in part of a flexible (non-rigid) polymer since the hydrostatic pressure of the liquid reaction (growth) medium present within the vessel together with the pressure of the sparging oxygen or oxygen containing gas will enable even a bag made of non-rigid polymer to substantially retain its annular shape. Suitable rigid polymers include, but are not limited to, USP Class VI approved polycarbonate and polystyrene. Suitable flexible polymers include, but are not limited to, low density polyethylene and ethylene/vinyl acetate copolymer.

Figure 3C:
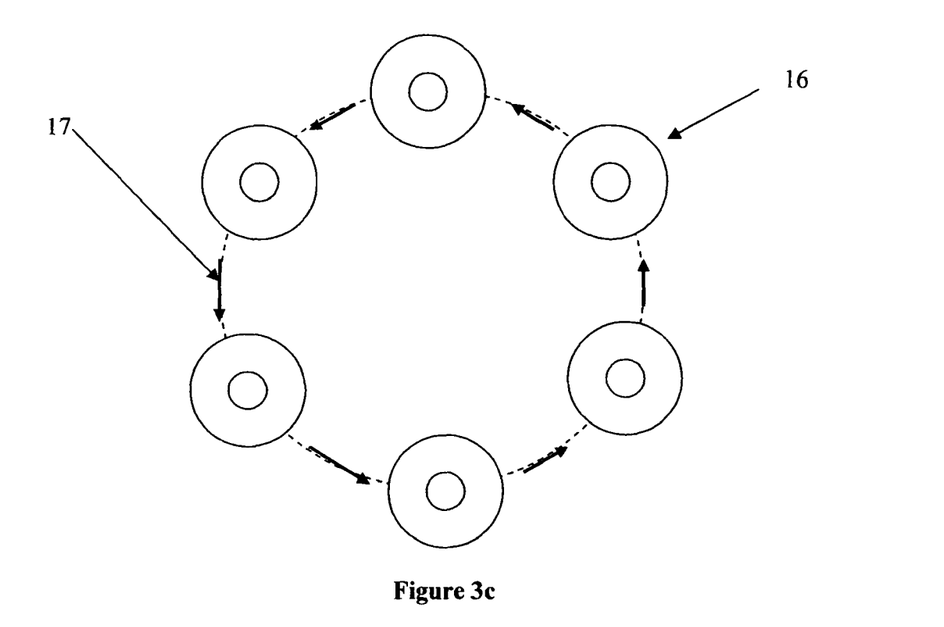
FIG. 3c shows how the bioreactor of the present invention achieves its enhanced mixing via orbital motion (in this case moving counterclockwise indicated as 16) which creates a travelling wave of the growth medium present in the bioreactor vessel (17).

In FIG. 3a, element 2 is a platform equipped with an electric motor or other drive means (not shown) which moves in an orbital motion as indicated by arrow 3 and as further shown in FIG. 3c. This orbital motion, combined with the toroidal shape of the bioreactor, sets up a traveling wave in the bioreactor growth medium. This traveling wave provides both effective mixing and oxygenation of the contents. It should be noted that in the case of a toroidal vessel whether having vertical or curved walls, the liquid motion will follow a pure traveling wave. In both cases, the exact liquid motion can be modeled using computational fluid dynamics.

Additionally, single-use bioreactor vessel 1 can suitably be equipped with one or a plurality of input ports (one shown as 4 in FIG. 3a) for process feedstock inputs (e.g.: 10 pH buffers, glucose etc.), and/or also for pre-inserted and pre-calibrated sensors (e.g., to measure dissolved oxygen, pH, dissolved $CO_2$ and the like). These sensors can be either traditional electrochemical sensors and/or disposable and pre-calibrated optical sensors. It is generally more efficacious to have the sensors pre-calibrated in order to avoid breaking the sterile barrier on the bioreactor. Optical probes are available that can be both pre-calibrated and can be gamma irradiated while mounted in the bioreactor. The ability to use gamma radiation allows the pre-calibrated sensors to be inserted in the bioreactor and the entire assembly subsequently sterilized. Port 5 denotes the exit port for removal of gaseous reaction by-products. In FIG. 3*a* 7 denotes a light source such as a bank of visible or UV light emitting LEDs that can be utilized to promote the growth of plant or algae culture or transiently activate certain genes for multi-drug production from a single cell platform. The lighting is shown on the top, but this is not a necessity; the illumination can additionally or alternatively come from the sides and/or even the bottom of the vessel provided only that the growth media receives enough illumination to enhance photosynthesis or gene activation depending on the purpose of the growth run and the cell being grown. Ideally the LEDs will have a spectrum that is matched to the absorption spectrum of the species being grown. LEDs are now available from the ultra-violet through the near infrared (e.g.: http://www.marktechopto.com/) so matching to the absorption spectrum of the species under study can be easily done. Additionally, the surface of the bioreactor on which the LED's are mounted needs to be sufficiently transmitting in this region to allow the light to pass through to the interior of the bioreactor.

The bioreactor vessel walls (outer and optional inner surfaces) define a structure that will have a resonant frequency which is determined by the particular configuration (size and shape) of the bioreactor. The resonant frequency of the bioreactor can be readily calculated knowing that the traveling wave must reproduce itself in phase every round trip (*Hydrodynamics*, Horace Lamb and Russ Caflisch, First Cambridge University Press, 1997). Once this frequency has been determined the bioreactor can be rotated with this circular frequency to thereby set-up resonant traveling wave motion of the fluid (growth medium) inside. The wave amplitude will be chosen depending on the level of mixing and agitation needed.

In FIG. 3*b* the top view, 10, of the bioreactor is shown along with the square or alternatively circular cross sections 11 and 12 respectively.

Figure 4:
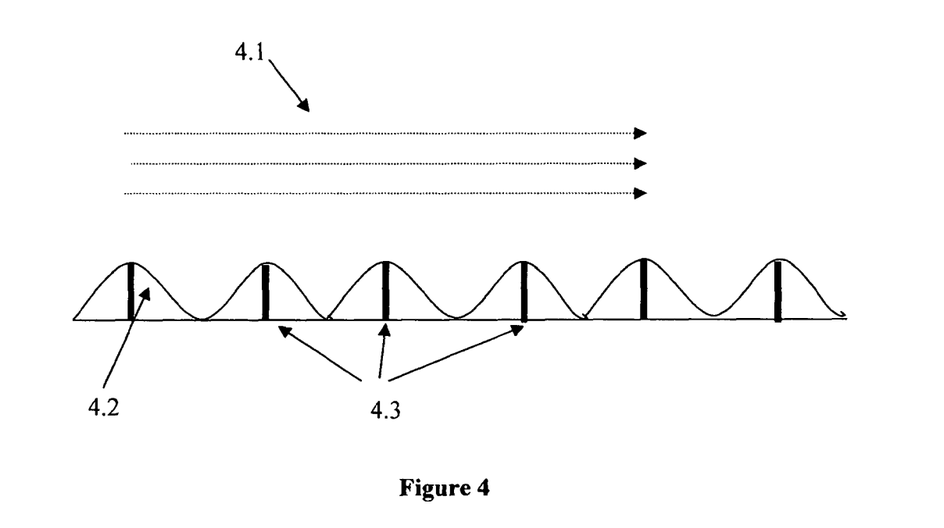
Figure 5:
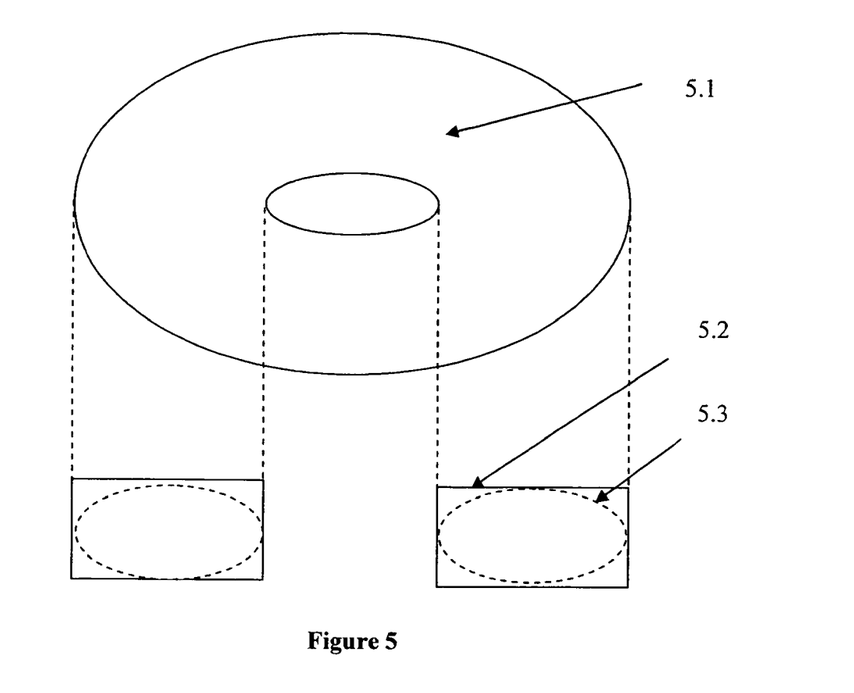
FIG. 5 shows a view of an alternative configuration for a bioreactor vessel in accordance with the present invention where the bioreactor is toroidal but oval in cross-section rather than circular. Again, the vessel can have a cross-section that is either substantially rectangular (5.2) or circular (5.3).

It is possible to further enhance the mixing and sparging efficiency of the bioreactor vessel of the present invention shown in FIG. 4 by providing a textured surface on the inner floor (bottom) and/or wall surfaces of the vessel (i.e., a surface which is in contact with the growth medium). This texturing can be achieved using baffles, ridges, bumps and/or other upstanding protuberances as shown in FIG. 4, which are preferably pre-molded on all or a part of the inner surface of the vessel. The sparging of the reaction medium is preferably accomplished in this design by bringing the oxygen or air into the bioreactor through a multitude of orifices in the floor and/or walls of the vessel. These orifices can be in the protuberances in the texturing or separate from them. In FIG. 4, the flow direction of the fluid in the annular vessel is indicated as 4.1, (which corresponds to arrow 3 in FIG. 4), the textured surface on the inner wall and/or floor surface of the vessel (the textured surface being shown here for simplicity to have an approximately sinusoidal shape pattern) is indicated as 4.2, and the sparge orifices are indicated as 4.3.

The optimal patterning (e.g., size, shape and frequency) will be a function of the size of the reactor, the velocity, viscosity, and nature of cell platform and its associated optimized growth medium. The particular patterning which provides optimal agitation can be determined through finite element analysis studies (www.fluent.com) or through empirical experiment. These studies generally include mixing studies as a function of time or number of agitation cycles. Additional computational studies that employ Henry's law (p. 384, *General Chemistry*, $2^{nd}$ *Edition*, Donald A. McQuarrie and Peter A. Rock, W. H Freeman and Company, New York, 1987) to model oxygen transfer or calculate the oxygen transfer rate are possible. These studies require the finite element analysis code to take into account the surface area of the bubbles created during sparging. For example, a higher number of bubbles having decreased size will increase the surface area available for oxygen transfer.

In FIG. 4, the sparging gas (normally air or oxygen) is suitably brought to the bioreactor using tubing through the sparge orifices 4.3 which preferably will have a fluid diode or hydrophobic filter at or near its end that allows the sparging gas to flow into the bioreactor, but prevents the liquid (reaction medium) from draining out of the bioreactor vessel through said tubing. The aforementioned texturing of the floor and/or walls therefore does not preclude bringing the sparge gas into the vessel through the floor, top, and/or walls of the vessel. This type of sparging, combined with the traveling wave motion induced by the orbital movement of the vessel, ensures that the cells or microbes in the bioreactor have access to sufficient feed and oxygen to achieve optimal total cell density and/or maximize product yield.

Figure 6:
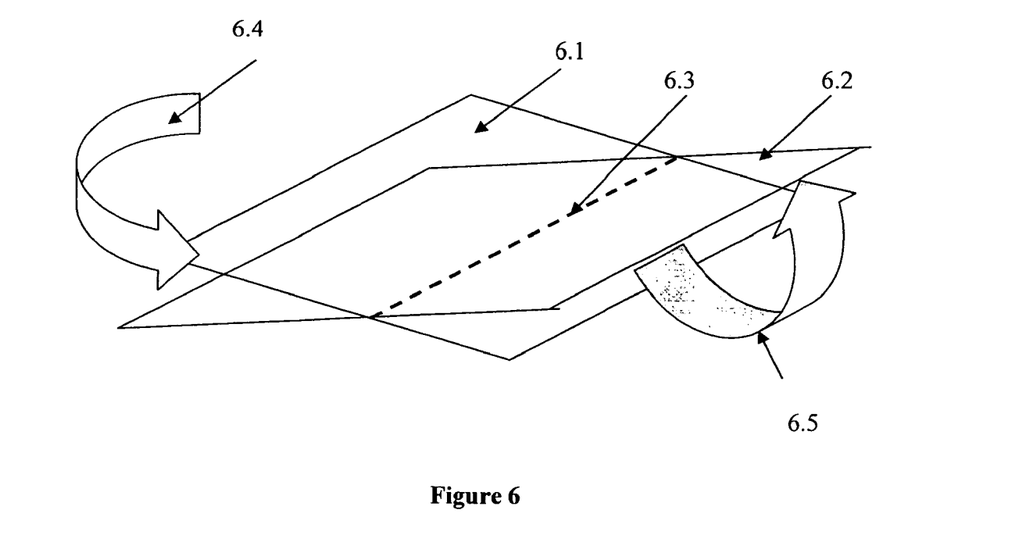
FIG. 6 shows an embodiment of the present invention which provides for multi-directional motion (i.e., both orbital and rocking) of the bioreactor vessel of the present invention shown in FIG. 3a, with the X and Y axes shown.

It should also be noted that the motion in direction FIG. 3*a* is only shown as orbital, but can also involve rocking in either the X or Y axis (or both) and thereby be a two-dimensional or three-dimensional motion, which can be readily tailored to work in conjunction with the bioreactor dimensions. Such multi-directional motion is shown in FIG. 6 where 6.1 and 6.2 are the plane of the platform when rocked about axis 6.3. The platform holding the bioreactor can also be orbited in one direction according to 6.4, or agitated in both directions as per 6.5. This motion can also be a reciprocating motion where the direction of rotation of the motor which causes the vessel to orbit is periodically reversed. This periodic reversal in the direction of the vessel's orbit can be used to cause more vigorous agitation if/when required during the growth process.

What is claimed is:
1. An apparatus comprising:
 (a) a hollow toroidal bioreactor vessel having an interior bounded by an inner surface, a textured surface being arranged on at least a portion of the inner surface, the textured surface having a sinusoidal shape pattern and being comprised of a plurality of upstanding protuberances, the toroidal bioreactor vessel further comprising a plurality of tubes coupled to at least a portion of the inner surface of the toroidal bioreactor vessel, wherein the plurality of tubes are configured for sparging gas into said toroidal bioreactor vessel, wherein one or more of the plurality of tubes is coupled to one or more of a bottom, a top, or a side-wall of the toroidal bioreactor vessel; and (b) a drive including a motor driven platform, wherein when the toroidal bioreactor vessel rests on the motor driven platform and a fluid is disposed within the interior of the toroidal bioreactor vessel, the drive is configured to move the platform orbitally such that there is a resonant frequency traveling wave of the fluid orbiting in one direction in the interior of the toroidal bioreactor vessel when a particular orbital speed is imparted to the toroidal bioreactor vessel, and wherein the orbiting direction of the traveling wave of the fluid is parallel to a direction of periodic oscillation of the sinusoidal shape pattern of the textured surface, wherein at least some of the plurality of tubes extend through the plurality of upstanding protuberances of the textured surface.

2. The apparatus in accordance with claim 1, wherein the textured surface is located on a bottom of the toroidal bioreactor vessel.

3. The apparatus in accordance with claim 1, wherein the textured surface is located on a side-wall of the toroidal bioreactor vessel.

4. The apparatus in accordance with claim 1, wherein the textured surface is located on both the bottom of the toroidal bioreactor vessel and the side-wall of the toroidal bioreactor vessel.

5. The apparatus in accordance with claim 1, wherein the plurality of tubes is coupled to the side-wall of the hollow toroidal bioreactor vessel.

6. The apparatus in accordance with claim 1, wherein operation of the drive moves the platform both orbitally and in a rocking motion.

7. The apparatus in accordance with claim 1, wherein when in operation, the drive is configured to move the toroidal bioreactor vessel in a reciprocating motion to cause the fluid to orbit in a reversed direction.

8. An apparatus comprising:
(a) a hollow bioreactor vessel comprising:
an interior bounded by an inner surface;
a textured surface arranged on the inner surface, the textured surface comprising a plurality of upstanding protuberances; and
a plurality of tubes coupled to the inner surface and extending through the plurality of upstanding protuberances of the textured surface, the plurality of tubes being configured for sparging a gas into the interior of the bioreactor vessel; and
(b) a drive including a motor driven platform, the bioreactor vessel being disposed on the motor driven platform, the drive being configured to move the platform orbitally.

9. The apparatus in accordance with claim 8, wherein when a fluid is disposed within the interior of the bioreactor vessel and the drive is activated, the drive moves the bioreactor vessel such that there is a resonant frequency traveling wave of the fluid orbiting in one direction in the interior of the bioreactor vessel when a particular orbital speed is imparted to the bioreactor vessel, and wherein the textured surface, the plurality of tubes, and the traveling wave of fluid are configured to enhance aeration and mixing efficiency of the fluid.

10. The apparatus in accordance with claim 8, wherein the textured surface is located on a bottom of the bioreactor vessel.

11. The apparatus in accordance with claim 8, wherein said bioreactor vessel is a hollow toroidal bioreactor vessel and includes at least one exit port for removal of gaseous by-products.

12. The apparatus in accordance with claim 8, further comprising a plurality of input ports for inserting sensors or process feedstock inputs into the bioreactor vessel.

\* \* \* \* \*